(12) United States Patent
Acker et al.

(10) Patent No.: US 7,779,840 B2
(45) Date of Patent: Aug. 24, 2010

(54) VENTILATOR BREATH CONDENSATE SAMPLER AND METHOD OF COLLECTING A BREATH CONDENSATE SAMPLE

(75) Inventors: Jaron M. Acker, Madison, WI (US); Kristopher J. Bilek, Madison, WI (US)

(73) Assignee: General Electric Company, Schenectady, NY (US)

( * ) Notice: Subject to any disclaimer, the term of this patent is extended or adjusted under 35 U.S.C. 154(b) by 1099 days.

(21) Appl. No.: 11/425,417

(22) Filed: Jun. 21, 2006

(65) Prior Publication Data

US 2008/0009761 A1    Jan. 10, 2008

(51) Int. Cl.
*A62B 7/02* (2006.01)
*A61B 5/0971* (2006.01)

(52) U.S. Cl. .............................. 128/204.16; 128/205.12; 600/532; 600/543

(58) Field of Classification Search ............ 128/204.15, 128/204.16, 104.18, 204.21, 205.12, 206.15; 600/529, 532, 543
See application file for complete search history.

(56) References Cited

U.S. PATENT DOCUMENTS

| | | | | |
|---|---|---|---|---|
| 3,613,665 | A * | 10/1971 | Gorsuch | 600/543 |
| 5,042,501 | A * | 8/1991 | Kenny et al. | 600/532 |
| 5,101,821 | A | 4/1992 | Carie, Jr. | |
| 5,465,728 | A * | 11/1995 | Phillips | 600/543 |
| 5,467,776 | A * | 11/1995 | Hamilton | 600/543 |
| 5,694,924 | A * | 12/1997 | Cewers | 128/204.21 |
| 5,826,575 | A * | 10/1998 | Lall | 128/205.12 |
| 6,148,657 | A * | 11/2000 | Satoh et al. | 73/23.35 |
| 6,582,376 | B2 * | 6/2003 | Baghdassarian | 600/543 |
| 2004/0138577 | A1 | 7/2004 | Kline | |
| 2004/0162500 | A1 | 8/2004 | Kline | |
| 2006/0266353 | A1 * | 11/2006 | Yamada et al. | 128/201.13 |
| 2007/0173731 | A1 * | 7/2007 | Meka et al. | 600/543 |

OTHER PUBLICATIONS

"Breath Condensate Measurements", Dr. Michael Rothe, FILT Lung and Thoraxdiagnostic Ltd., pp. 13-16, admitted prior art, 2006.
"H202 as a Component of Breath Condensate", Bitterling et al., Klinic Bad Reichenhall, pp. 11-12, admitted prior art, 2006.
"Non-Invasive Monitoring of Airway Inflammation: Exhaled breath condensate", Barnes et al., National Heart and Lung Institute, pp. 3-6, admitted prior art, 2006.
"Constituent Parts of Breath Condensate . . . and methods for standardization", Dr. Michael Rothe, FILT Lung and Thoraxdiagnostic Ltd., p. 7, admitted prior art, 2006.
"Providing Oxygen Therapy During Exhaled Breath Condensate Collection Using the RTube", Walsh et al., University of Virginia Health System, admitted prior art, 2006.

* cited by examiner

*Primary Examiner*—Danton DeMille
(74) *Attorney, Agent, or Firm*—Andrus, Sceales, Starke & Sawall, LLP (57) ABSTRACT

A breath condensate sampler for use with a mechanical ventilator, the breath condensate sampler includes an airflow valve, a condensate formation tube, a condensate trap, and a condensate collection receptacle. The airflow valve directs air from the expiratory limb into the condensate formation tube wherein the condensate portion of exhaled gases are separated from the gaseous portion of the exhaled gases. A method of collecting a breath condensate sample is also herein disclosed.

21 Claims, 5 Drawing Sheets

VENTILATOR BREATH CONDENSATE SAMPLER AND METHOD OF COLLECTING A BREATH CONDENSATE SAMPLE

FIELD OF THE INVENTION

The present invention relates to the field of non-invasive diagnostic devices. More specifically, the present invention relates to the non-invasive monitoring of respiratory health of a patient receiving mechanical ventilator support.

BACKGROUND OF THE INVENTION

Exhaled air is an effective way for our body to remove unwanted compounds. Each breath contains a variety of compounds produced as a byproduct of cellular metabolism, for example, carbon dioxide. The breath may also contain toxins that the body is trying to remove from its system. Additionally, as the breath leaves the lungs, an aerosol is formed comprising the contents of the bronchioalveolar lining.

Analysis of exhaled air can be used as a non-invasive method of diagnosis. Two examples of this that have found their way into common usage are the breathilizer test, which measures the percentage of alcohol present in the subject's exhaled air, which is indicative of the percentage of alcohol in the patient's blood, and the detection of acetone in the patient's breath giving the exhaled air a "fruity" smell, which indicative of diabetic ketoacidosis. Additionally, the non-gaseous portion of the breath may be analyzed to receive an indication of the composition of the aforementioned bronchioalveolar lining. This lining comprises antioxidants, proteins, epithelials, and a variety of other compounds that form an initial line of defense against inhaled oxidants (environmental pollutants) as well as airborne pathogens. By separating this condensate from the rest of the exhaled gases and performing an analysis of its content, the analysis may be used to gain a snapshot of the contents of the patient's bronchioalveolar lining.

The analysis of exhaled air can be used as a non-invasive diagnostic tool to identify what is in the patient's lungs. Commonly, this analysis will identify the presence of inflammation in the patient's lungs and the elevated presence of particular compounds can identify the source of this inflammation. Analysis of the exhaled air provides a system of early detection for ailments such as bacterial or viral infections as well as the early stages of lung cancer. Continued monitoring of a patient by collecting exhaled breath concentrate (EBC) samples and analyzing their content can provide a useful tool for detecting the progress of a disease and/or the treatment of the disease. This may be used for the treatment of chronic diseases such as allergies, cystic fibrosis (CF), and chronic obstructive pulmonary disease (COPD), but may also be used for monitoring the treatment of curable diseases such as bronchitis or pneumonia due to bacterial or viral infection.

An example of one such compound that may be monitored are isoprostanes, which are indicative of oxidative stress on the lungs. Increased levels of isoprostanes, particularly 8-isoprostane, have been shown to be indicative of asthma, CF, and COPD. Another example of a compound found in EBC that may be monitored for are vaso-active peptides, the presence of which are indicative of airway inflammation with the levels of these peptides being related to the severity of the inflammation. An example of a further type of analysis that may be performed on EBC is a UV-spectra of the EBC as the integral of the UV-spectra appears to be correlated to the surface area of the lung being used. However, these examples are not meant to be limiting as further analysis for compounds such as proteins, T-bars, hydrogen peroxide, DNA, and many others may be monitored to produce useful diagnostic information.

The collection of exhaled breath concentrate (EBC) presents a variety of challenges as the patient must generally go through several respiratory cycles in order to accumulate a sufficient amount of EBC for the required analysis. The collection of EBC currently requires the patient to be spontaneously breathing. Additionally, challenges exist in the condensing of the EBC out of the patient's breath while maintaining the EBC free from outside contaminants. Often a cooling mechanism is used to facilitate the condensing of the EBC from the exhaled breath, since cooling increases the efficiency of the condensating, thus requiring fewer respiratory cycles to obtain the desired sample amount.

Current EBC collectors are generally in the form of handheld devices, and these devices are cumbersome to use with a patient who is receiving mechanical ventilation. Beyond the fact that current handheld devices require the patient to be not only spontaneously breathing, but spontaneously breathing with the necessary force to over the resistance of the handheld device. The use of the handheld device requires temporarily taking the patient off of the ventilator, waiting the sufficient number of respiratory cycles while the handheld device obtains an EBC sample, then placing the patient back on ventilatory support. This task becomes nearly impossible if the patient is receiving mechanical ventilation through a more invasive type of patient connection, such as an endotrachial tube. The currently available EBC collection devices do not offer any integration ability with the breathing circuit of a mechanical ventilator.

Therefore, it is desirable in the field of respiratory care to provide an EBC sampler that may be used in conjunction with a patient receiving respiratory support via a mechanical ventilator without the patient being disconnected from the mechanical ventilator.

SUMMARY OF THE INVENTION

By the present invention and the method of treatment, EBC may be collected from a patient currently receiving mechanical ventilatory support. By an embodiment of the present invention, a breath condensate sampler is made integral with the expiratory limb of the mechanical ventilator. The EBC sampler comprises a valve whereby upon manual or automatic selection exhaled air may be diverted from the expiratory limb into the EBC sampler where the EBC is removed from the expired breath and the remaining gaseous portion of the expired breath is returned to the expiratory limb or vented to the outside air. Upon removing the EBC from the gaseous portion of the expired breath, the EBC sampler of the present invention collects the EBC, in a collection receptacle. A volume indicator allows for the determination of the amount of EBC that has been collected by identifying when the desired volume has been reached. Once the desired volume has been accumulated, the valve of the EBC sampler may be closed whereby no more expired breath is directed into the EBC sampler and the EBC sample may be removed for analysis.

BRIEF DESCRIPTION OF THE DRAWINGS

The drawings illustrate the best mode presently contemplated of carrying out the invention. In the drawings.

DETAILED DESCRIPTION OF THE DRAWINGS

Figure 1:
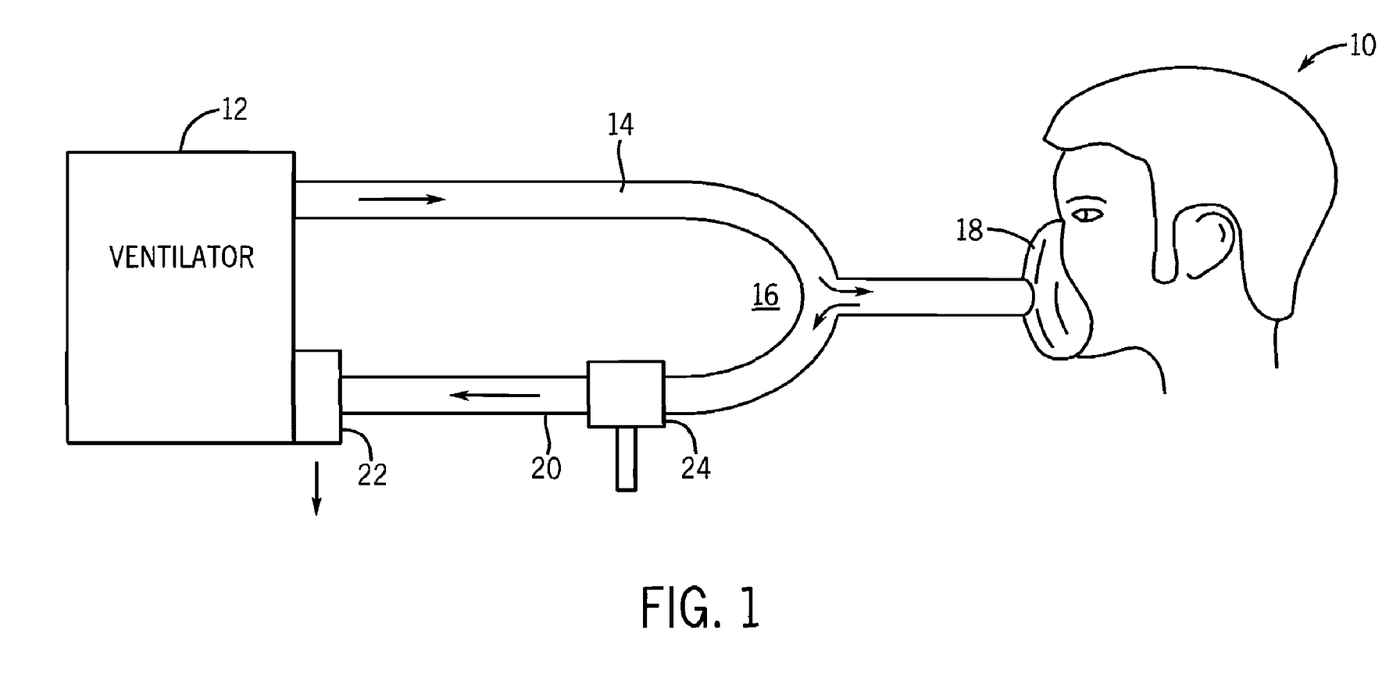
FIG. 1 is a schematic diagram of an embodiment of the present invention showing a topical ventilator system connected to the device of the present invention.

FIG. 1 is a depiction of a patient 10 receiving mechanical ventilatory support from a ventilator 12. In typical ventilator operation, the ventilator 12 produces a delivery of medical gases which are predominantly air in a pressurized state through the inspiratory limb 14 of the breathing circuit 16 to the patient 10. The pressure generated by the ventilator 12 is sufficient to overcome the natural resistance of the patient's lungs, thereby delivering a breath of air to the patient through the patient connection 18. As the ventilator reduces the generated pressure, the natural compliance of the patient's lungs forces the delivered air out of the patient 10 through the patient connection 18 and into the expiratory limb 20. When the expired breath reaches the expiration valve 22, the expired gases are released to the ambient air. The exhaled breath condensate (EBC) sampler 24 of the present invention is disposed in fluid connection with the expiratory limb 20. The exact location of the EBC sampler may be anywhere along the expiratory limb 20 from a location proximal to the patient 10 such as the patient connection 18, to a location distal from the patient such as on the outlet of the expiration valve 22. The EBC sampler 24 may be attached to the ventilator 12 such that the EBC sampler 24 is held in a fixed position with the expiratory limb 20 leading to and from the EBC sampler 24.

Figure 2:
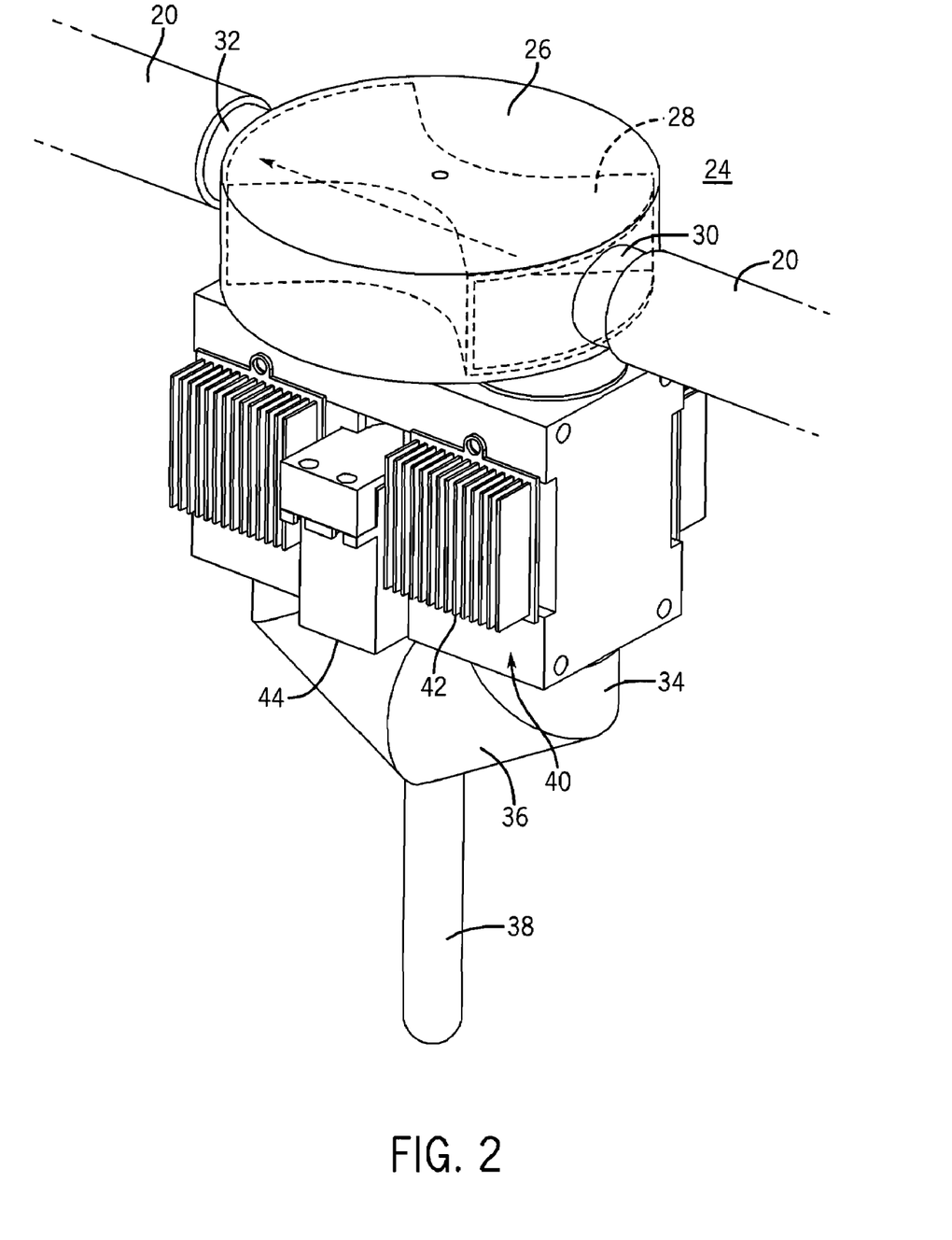
FIG. 2 is an embodiment of the present invention.

FIG. 2 depicts an embodiment of the EBC sampler 24 of the present invention. The EBC sampler 24 comprises an airflow valve assembly 26 that comprises a stopcock 28, an inlet 30, and an outlet 32. Airflow valve assembly 26 may comprise any of a variety of valves within the present invention as any suitable type of valve that can direct gas flow in two different directions to correspond with two different valve positions may be used. However, for the purposes of example, a hollow stopcock 28 is used in all descriptions of the airflow valve assembly 26, but is not meant to be limiting to this embodiment. As depicted in FIG. 2, the EBC sampler 24 is inserted into the expiratory limb 20 with the expiratory limb 20 connecting to both the inlet 30 and outlet 32 of the airflow valve assembly 26. The EBC sampler 24 further comprises a U-shaped condensate formation tube 34 and a condensate trap 36. Condensate collection receptacle 38 is connected to the condensate trap 36 and collects the condensate that is in the condensate trap 36.

A cooling sleeve 40 surrounds the condensate formation tube 34. The cooling sleeve 40 is cooled by cooling apparatus 42. A motor 44 is used to operate the airflow valve assembly 26 by turning the stopcock 28 to a desired position. The control of the cooling apparatus 42 and the positioning of the stopcock 28 is performed by a controller which may comprise a microprocessor (not shown).

Referring now to FIGS. 1 and 2, the operation of the present invention is as follows. In the course of a normal respiration cycle of a patient receiving mechanical ventilation, the ventilator 12 delivers medical gas to the patient 10 via the inspiration limb 14 and patient connection 18. When the patient 10 expires these gases, the expired gases flow back out through the patient connection 18 and into the expiratory limb 20 in which for this description the EBC sampler 24 is integrally disposed. However, in an alternative embodiment, the inlet 30 of the EBC sampler may be connected to the expiration valve 22 and the outlet 32 of the EBC is then vented to the ambient air.

Figure 3A:
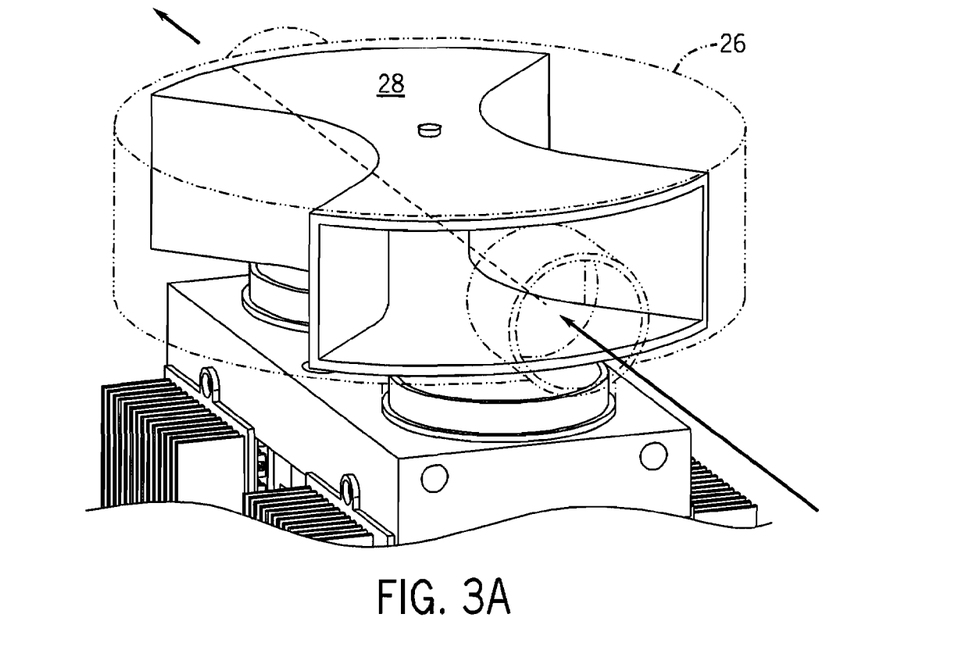
FIG. 3 is a cutaway view of an embodiment of the present invention depicting the flow of air through the invention.
Figure 3B:
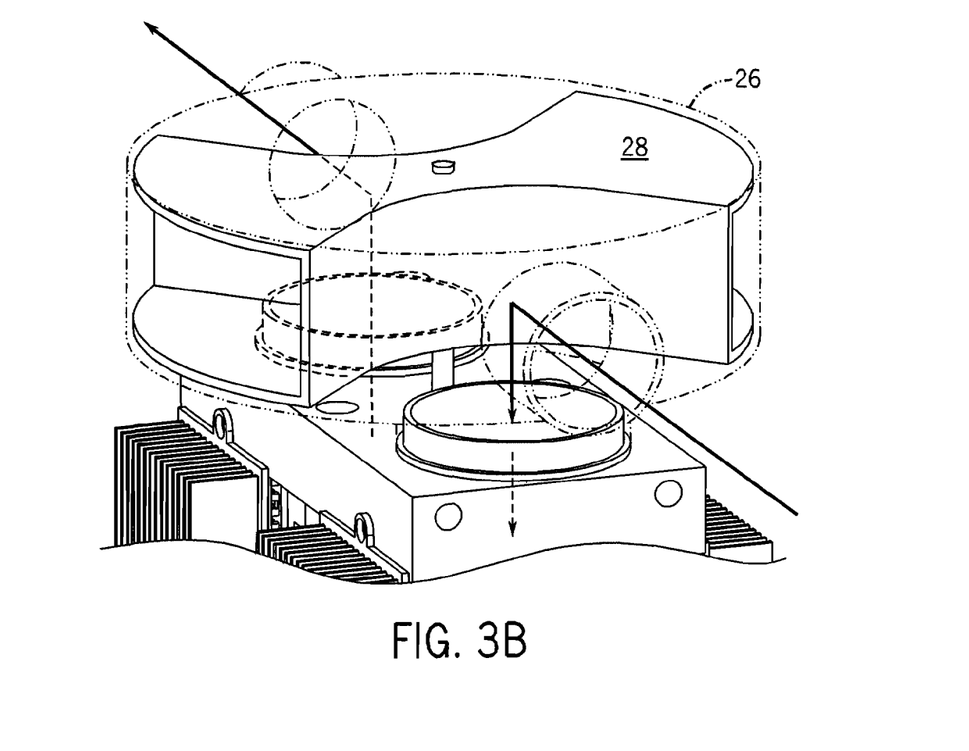

When the airflow valve assembly 26 is in the normal ventilation mode, the stopcock 28 is oriented as depicted in FIG. 3A such that the expired breath in the expiratory limb 20 flows through the inlet 30, through a hollow portion of the stopcock 28, and out the outlet 32 back into the expiratory limb 20. When it is desired to take a sample of the exhaled breath concentrate (EBC), a signal is sent by the controller to the motor 44 to turn the stopcock 90 degrees such that the orientation of the stopcock 28 is that as is depicted in FIG. 3B. It is understood that by this present invention, the decision to take an EBC sample may be performed manually by a clinician or may be part of a larger automated patient monitoring system that would perform EBC sampling at regular specified intervals. The automated system may be an integral part of the ventilator controller, or may be a part of a stand-alone device.

Figures 4A, 4B:
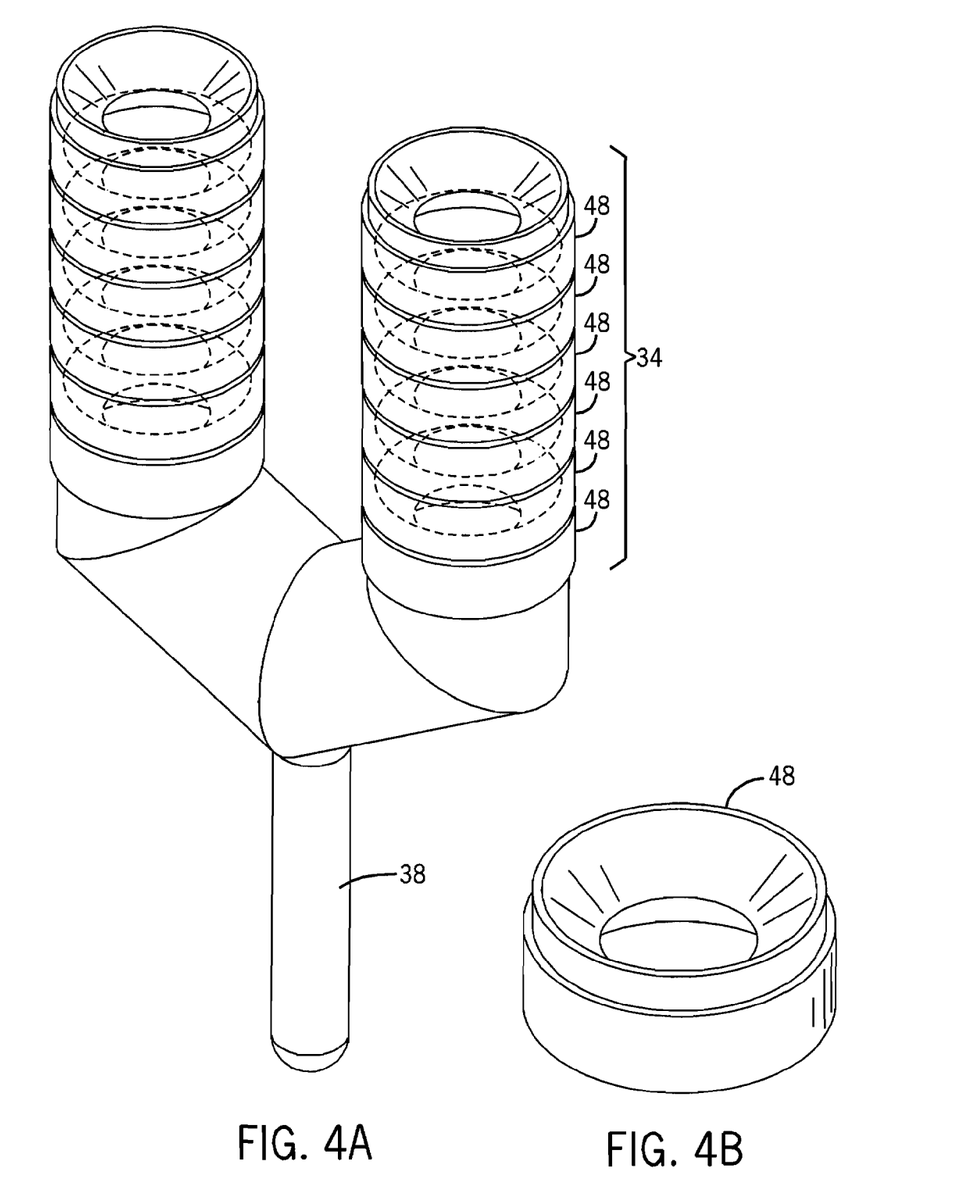
FIG. 4 is a depiction of the condensate collection tubes and the condensate collection receptacle.

Once the stopcock 28 has been positioned so that the expired breath will flow through the condensate formation tube 34, the expired air will enter the condensate formation tube 34 as depicted in FIG. 4. The condensate formation tube 34 may be comprised of a thermally conductive liquid crystalline polymer or similar material. The advantage of these plastics is that they have thermo-conductive properties similar to that of glass. The advantage to having a plastic tube is for ease of production, ability to be re-used after sterilization, and reduced risk of breaking. The composition of the formation tube should not be read as limited to the aforementioned liquid crystalline polymer composition, but rather extends to any thermally conductive material, including metals. Additionally, the condensate formation tube 34 may also be disposable in construction. The formation tubes 34 may also comprise a plurality of tube components 48. These tube components may be funnel or ridge shaped, or any shape that facilitates the purpose of increasing the surface area of the condensate formation tube 34 upon which the condensate will form and to direct the condensate to fall downward down the formation tube 34. In an alternative embodiment of the present invention, formation tubes 34 may comprise tube components 48 that may be molded individually and assembled by means of snapping or screwing together, or may be molded as a single component.

Referring back to FIG. 2, the cooling sleeve 40 surrounding the condensate formation tubes 34 and the cooling apparatus 42 are added to the system to facilitate the collection of EBC. Upon leaving the body, expired air is at a temperature of approximately 37 degrees C., and only 6.4 percent of the water vapor will condense into water at that temperature. Therefore, proper EBC collection will be obtained at temperatures between 10 degrees C. and −10 degrees C. where 80 to 95 percent of the water vapor, and included EBC, will condense. As such, the cooling sleeve 40 and cooling apparatus 42 play an important role in greatly increasing the efficiency of the EBC sampler 24. The cooling apparatus 42 may be any device, or combination of devices that will facilitate the cooling of the cooling sleeve 40 and the formation tubes 34. One embodiment of the present invention may include the combination of a thermal electric device such as a Peltier device and heat sinks. Other potential cooling devices may be refrigeration technology, an endothermic reaction, or simply the use of a larger cooling sleeve filled with ice, but any other suitable mechanism to provide the necessary described cooling of the condensate formation tube would be suitable in the present invention.

Once the expired breath has passed through the condensate formation tube 34 and the EBC has been pulled from the breath, the EBC is pulled by gravity into the condensate trap 36 and directed into the condensate collection receptacle 38. In an embodiment of the present invention, the condensate collection receptacle 38 is a test tube or assay vial. This collection receptacle 38 will collect and store the necessary volume of EBC sample for a proper analysis. A sensor (not pictured) associated with the receptacle 38 may identify when the necessary sample size (0.25 ml-3 ml, typical) has been collected. In an embodiment of the present invention, once the desired volume of sample has been collected, the EBC sampler 24 will stop collecting EBC by rotating the stopcock 28 90 degrees to direct the airflow through the airflow assembly valve 26 and into the expiratory limb 20.

Once the EBC sample has been collected in the condensate collection tube 38, the composition of the EBC may be determined. The composition may be determined using a variety of clinical tests, including immunoassays. Alternatively, mass spectrometry and/or liquid or gas chromatography may be used to analyze the composition. It is understood that any standard laboratory technique for determining the composition of a biological sample may be used in analyzing the EBC sample in accordance with the present invention. It is further understood that other sensors capable of collecting information from the exhaled air, such as pH sensors, may be disposed within an embodiment of the EBC sampler of the present invention.

Other considerations are to be viewed within the present invention for maintaining the quality the EBC sample and resulting analysis is that for some biological substances, it is necessary that the sample be kept at a cold temperature and must be analyzed within a short time duration from sample collection. For example, while some biological components of the EBC sample such as leukotriene $E_4$, chloride, and nitrate will last in a lab under cold conditions for over six months, other substances such as hydrogen peroxide ($H_2O_2$) will only last in the EBC sample for approximately three hours. As such, in an embodiment of the present invention, the condensate collection receptacle 38 will be connected directly to an apparatus for determining the composition of the EBC sample. This would facilitate the automation of the entire EBC sampling system, thus enabling the system to provide a clinician with regularly scheduled EBC content analysis at the patient's bedside. After the EBC has been removed from the expired breath passing through the EBC sampler 24, the condensate formation tube 34 directs the expired breath out through the outlet 32 and back into the expiratory limb 20 where the expired breath will be directed to the expiration valve 22 and released to the outside air. In an alternative embodiment of the present invention, the outlet 32 will release the expired breath to the outside air directly. As described previously, when the EBC sample has been fully collected, the controller will turn the stopcock 28 another 90 degrees such that the formation tube 34 has been blocked and the expired breath flows through the airflow assembly 26 as depicted in FIG. 3A.

Figure 5:
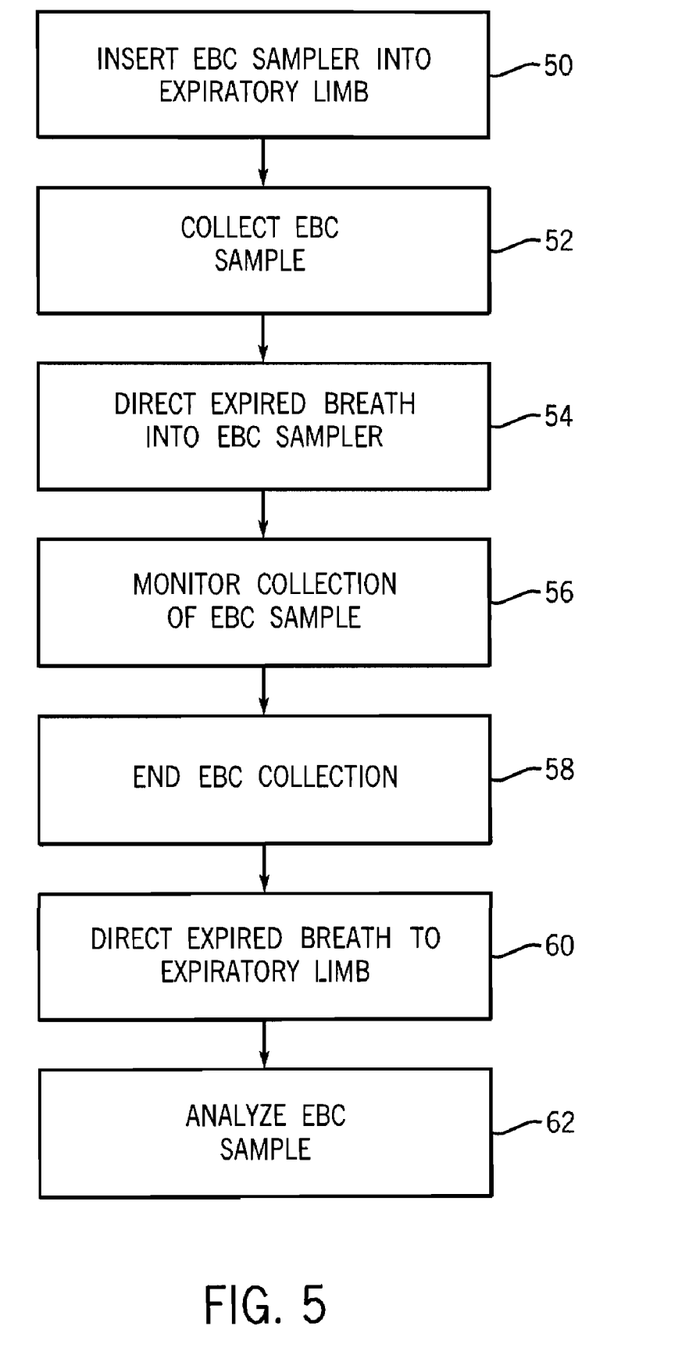

Now referring to FIG. 5 as a description of a method of collecting an EBC sample in conjunction with the device of the present invention. This method provides a way for a clinician to collect an EBC sample from a patient that is currently receiving mechanical ventilatory support. This patient may be making spontaneous breath attempts or may be receiving full mechanical ventilation. First, the clinician will insert the EBC sampler into fluid connection with the expiratory limb in step 50. The clinician may do this upon initial setup before placing the patient on the ventilator, or may temporarily take the patient off the ventilator to insert the EBC sampler. Once the EBC sampler has been inserted in the expiratory limb, the EBC sampler is activated to begin collecting an EBC sample in step 52. This may be done manually by the clinician selecting to begin EBC collection or may be part of an automated system with predetermined time intervals between EBC sample collections. Upon activation of the EBC sampler 52, the EBC sampler begins shunting the expired breath into the EBC sampler in step 54. Next, the EBC sampler monitors the progression of the collection of the EBC sample in step 56. Upon the collection that reaches a predetermined threshold volume, the EBC sampler ends the EBC sample collection in step 58. Upon ending the EBC sample collection, the EBC sampler re-directs the flow of the expired breath back into the expiratory limb in step 60. Finally, the EBC sample is analyzed to determine the constituent concentrates within the EBC sample in step 62. This may be done using immunoassays, mass spectrographs or chromatography, but may also be performed using any of a variety of known laboratory techniques.

The above-described present invention presents distinct advantages over other systems known in the art. The system of the present invention is designed to be compatible with a mechanical ventilation system, thus providing the ability to perform an EBC collection on a patient who is receiving mechanical ventilation. Previous systems have required that the patient by spontaneously breathing and must be removed from mechanical ventilation in order to collect an EBC sample. By the present invention, a sample may be collected without removing a patient from mechanical ventilation support, and also may be collected from a patient that is not spontaneously breathing as the ventilation, support will drive the patient's respiratory cycle. The present invention also presents the advantage for use with a mechanical ventilator of isolating the expiratory limb of the mechanical ventilator from the rest of the components of the EBC sampler 24 when the EBC sampler 24 is not in use. This allows for the components of the EBC sampler that come in contact with the expired air from the patient, such as the collection formation tube 34, condensate trap 36, and condensate collection receptacle 38 to be removed and prepared for the collection of the next EBC sample. This preparation may include autoclaving or other sterilizing processes on these components, or the components may be disposable in their construction and therefore the clinician may dispose of them and replace the components.

Embodiments of the present invention also present the advantage of the potential for the automation of the EBC sampling and analysis process for a patient that is receiving mechanical ventilatory care. The automation of this process would present the advantage of quickly analyzing the EBC samples thereby maintaining the quality of the sample that is analyzed. Also, this would provide a quick analysis response to the clinician that may be displayed to the clinician along with any other monitored patient physiological parameter. Thus, the clinician would not have to deal with physically removing the sample and delivering it to a lab and waiting for a lab to process and return the results. Furthermore, the EBC sampler may be wired or wirelessly connected to the ventilator or a centralized hospital information system. Data collected by the EBC sampler may be transmitted to these locations for clinician use. The automated data collection and display would further enhance the care provided by the clinician by improving point of care information provided to the clinician.

This written description uses examples to disclose the invention, including the best mode, and also to enable any person skilled in the art to make and use the invention. The patentable scope of the invention is defined by the claims and may include other examples that occur to those skilled in the art. Such other examples are intended to be within the scope of the claims if they have structural elements that do not differ from the literal language of the claims, or if they include equivalent structural elements of insubstantial difference from the literal language of the claims.

Various alternatives and embodiments are contemplated as being with in the scope of the following claims, particularly pointing out and distinctly claiming the subject matter regarded as the invention.

What is claimed is:

1. A method of collecting a sample of breath condensate from a patient receiving mechanical ventilation via a mechanical ventilator, the method comprising the steps of:
   inserting a breath condensate sampler in fluid connection with an expiratory limb of the ventilator, the expiratory limb directing exhaled breath away from the patient;
   activating the sampler to collect a sample of breath condensate from the exhaled breath;
   cooling a condensate formation tube of the breath condensate sampler to a target temperature;
   shunting the exhaled breath from the expiratory limb into the condensate formation tube;
   condensing breath condensate from the exhaled breath as the exhaled breath passes through the condensate formation tube and back to the expiratory limb;
   collecting a breath condensate sample;
   ending the breath and condensate sample collection when the breath condensate sample reaches a threshold volume.

2. The method of claim 1 further comprising the step of analyzing the breath condensate sample to determine constituent concentrates of the breath condensate sample.

3. The method of claim 2 wherein collecting the breath condensate sample comprises directing the breath condensate sample into a breath condensate sample analysis device.

4. The method of claim 3 wherein the breath condensate sample analysis device is a mass spectrograph.

5. The method of claim 1 wherein the step of activating the sampler is performed automatically according to a pre-determined schedule of sample collections.

6. The method of claim 1 wherein the threshold volume is between 0.25 mL and 3 mL.

7. A breath condensate sampler for use with a mechanical ventilator delivering respiratory support to a patient via a breathing circuit, the breath condensate sampler comprising:
   an air flow valve configured to couple with the breathing circuit and to receive exhaled gases therefrom through an inlet, the air flow valve being movable between a first position that allows exhaled gases to flow from the inlet through the air flow valve and a second position that directs exhaled gases from the inlet into the breath condensate sampler;
   a condensate formation tube connected to the air flow valve, the condensate formation tube separates a condensate portion of the exhaled gases from a gaseous portion of the exhaled gases and directs the gaseous portion out of the breath condensate sampler;
   a cooling sleeve surrounding at least a portion of the condensate formation tube;
   a cooling apparatus coupled to the cooling sleeve such as to cool the cooling sleeve and the condensate formation tube, wherein the condensate formation tube further comprises a thermally conductive material;
   a condensate trap connected to the condensate formation tube, the condensate trap collects the condensate portion from the condensate formation tube; and
   a condensate collection receptacle connected to the condensate trap, the condensate collection receptacle accumulates the condensate portion of the exhaled gases.

8. The breath condensate sampler of claim 7, wherein the cooling apparatus further comprises a Peltier device and a plurality of heat sinks.

9. The breath condensate sampler of claim 7, wherein the cooling apparatus and the cooling sleeve cool the condensate formation tube to a temperature between ten degrees Centigrade and negative ten degrees Centigrade.

10. A breath condensate sampler for use with a mechanical ventilator delivering respiratory support to a patient via a breathing circuit, the breath condensate sampler comprising:
    an air flow valve configured to couple with the breathing circuit and to receive exhaled gases therefrom through an inlet, the air flow valve being movable between a first position that allows exhaled gases to flow from the inlet through the air flow valve and a second position that directs exhaled gases from the inlet into the breath condensate sampler;
    a condensate formation tube connected to the air flow valve, the condensate formation tube separates a condensate portion of the exhaled gases from a gaseous portion of the exhaled gases and directs the gaseous portion out of the breath condensate sampler;
    a condensate trap connected to the condensate formation tube, the condensate trap collects the condensate portion from the condensate formation tube; and
    a condensate collection receptacle connected to the condensate trap, the condensate collection receptacle accumulates the condensate portion of the exhaled gases;
    wherein the condensate formation tube further comprises a first condensate formation tube and a second condensate formation tube, the first and second condensate formation tubes being substantially vertical and connected to each other by the condensate trap, such that the exhaled gases are directed into the breath condensate sampler through the first condensate tube and out of the breath condensate sampler through the second condensate tube.

11. The breath condensate sampler of claim 10, further comprising surface area increasing tube components disposed within the first and second condensate formation tubes.

12. The breath condensate sampler of claim 11, wherein the tube components facilitate the gravitational accumulation of the condensate portion.

13. The breath condensate sampler of claim 12, wherein the tube components are downwardly directed annular flanges.

14. The breath condensate sampler of claim 10, wherein when the air flow valve is in the second position, the exhaled gases are directed through the first condensate formation tube, through the condensate trap, and through the second condensate formation tube before being directed out of the breath condensate sampler.

15. The breath condensate sampler of claim 14, further comprising a cooling apparatus coupled to the first condensate formation tube and the second condensate formation tube, the cooling apparatus cools the first and second condensate formation tube to a predetermined temperature.

16. The breath condensate sampler of claim 15 further comprising a volume indicator connected to the condensate receptacle, the volume indicator produces an indication of the volume of accumulated condensate portion.

17. A respiratory support system for providing respiratory support to a patient comprising:
    an inspiratory limb connected to the patient that delivers fresh gas to the patient;
    an expiratory limb connected to the patient that directs expired gas away from the patient;

an air flow valve connected in fluid communication with the expiratory limb, the air flow valve comprising an operational position that directs the expired gas into an inlet;

a first condensate formation tube connected to the inlet, the first condensate formation tube comprising a plurality of tube components that increase the surface area inside the first condensate formation tube, a condensate portion of the exhaled gases condenses on the plurality of tube components as the expired gas passes through the first condensate formation tube;

a condensate receptacle that accumulates the condensate portion;

a condensate trap connected to the first condensate formation tube and the condensate receptacle, the condensate trap collects the condensate portion from the first condensate formation tube and directs the condensate portion into the condensate receptacle; and a second condensate formation tube connected to the condensate trap and comprising a plurality of tube components that increase the surface area inside the second condensate formation tube, the second condensate formation tube receiving the expired gases from the first condensate formation tube and directs the expired gas back to the expiratory limb, the condensate portion of the exhaled gas condenses on the plurality of tube components in the second condensate formation tube as the expired gas passes through the second condensate formation tube.

18. The respiratory support system of claim 17 wherein the plurality of tube components of the first and second condensate formation tubes are of a shape as to facilitate the gravitational accumulation of the condensate portion.

19. The respiratory support system of claim 18 further comprising a cooling apparatus coupled to the first second condensate formation tubes, and the cooling apparatus controls the temperature of the first and second condensate formation tubes.

20. The respiratory support system of claim 17 wherein the air flow valve further comprises a closed position that fluidly isolates the first and second condensate formation tubes, the condensate trap, and the condensate receptacle from the expiratory limb.

21. The respiratory support system of claim 20 wherein the condensate receptacle is removable from the condensate trap.

* * * * *